(12) United States Patent
Rosell et al.

(10) Patent No.: US 11,156,831 B2
(45) Date of Patent: Oct. 26, 2021

(54) EYE-TRACKING SYSTEM AND METHOD FOR PUPIL DETECTION, ASSOCIATED SYSTEMS AND COMPUTER PROGRAMS

(71) Applicant: Tobii AB, Danderyd (SE)

(72) Inventors: Mikael Rosell, Danderyd (SE); Simon Johansson, Danderyd (SE); Johannes Kron, Danderyd (SE)

(73) Assignee: Tobii AB, Danderyd (SE)

( * ) Notice: Subject to any disclaimer, the term of this patent is extended or adjusted under 35 U.S.C. 154(b) by 0 days.

(21) Appl. No.: 16/732,113

(22) Filed: Dec. 31, 2019

(65) Prior Publication Data

US 2021/0199957 A1 Jul. 1, 2021

(51) Int. Cl.
| | |
|---|---|
| G06F 3/01 | (2006.01) |
| G02B 27/00 | (2006.01) |
| G02B 27/01 | (2006.01) |
| A61B 3/113 | (2006.01) |
| G06K 9/62 | (2006.01) |
| G06K 9/00 | (2006.01) |
| G06K 9/46 | (2006.01) |

(52) U.S. Cl.
CPC .......... *G02B 27/0093* (2013.01); *A61B 3/113* (2013.01); *G02B 27/017* (2013.01); *G06F 3/013* (2013.01); *G06K 9/0061* (2013.01); *G06K 9/4647* (2013.01); *G06K 9/4661* (2013.01); *G06K 9/6212* (2013.01)

(58) Field of Classification Search
CPC ... G02B 27/0093; G02B 27/017; A61B 3/113; G06K 9/6212; G06K 9/0061; G06K 9/4647
USPC ....................................................... 345/156
See application file for complete search history.

(56) References Cited

U.S. PATENT DOCUMENTS

| | | | |
|---|---|---|---|
| 10,213,105 B2* | 2/2019 | Sarkar | A61B 3/15 |
| 10,496,159 B2* | 12/2019 | Norden | G06F 21/32 |
| 2019/0045100 A1* | 2/2019 | Michishita | G06T 7/11 |

\* cited by examiner

*Primary Examiner* — Calvin C Ma
(74) *Attorney, Agent, or Firm* — Samuel I. Yamron

(57) ABSTRACT

An eye-tracking system for performing a pupil-detection process, the eye-tracking system configured to: receive image-data comprising a plurality of pixel-arrays, each pixel-array having a plurality of pixel locations and an intensity-value at each of the pixel locations; for each pixel location of a region of pixel locations: define an intensity-value-set comprising the intensity-values at the pixel location for two or more of the plurality of pixel-arrays; and determine the pixel location to be an excluded pixel location if the intensity-value-set does not satisfy an intensity condition; and exclude the excluded pixel locations from the pupil-detection process.

19 Claims, 8 Drawing Sheets

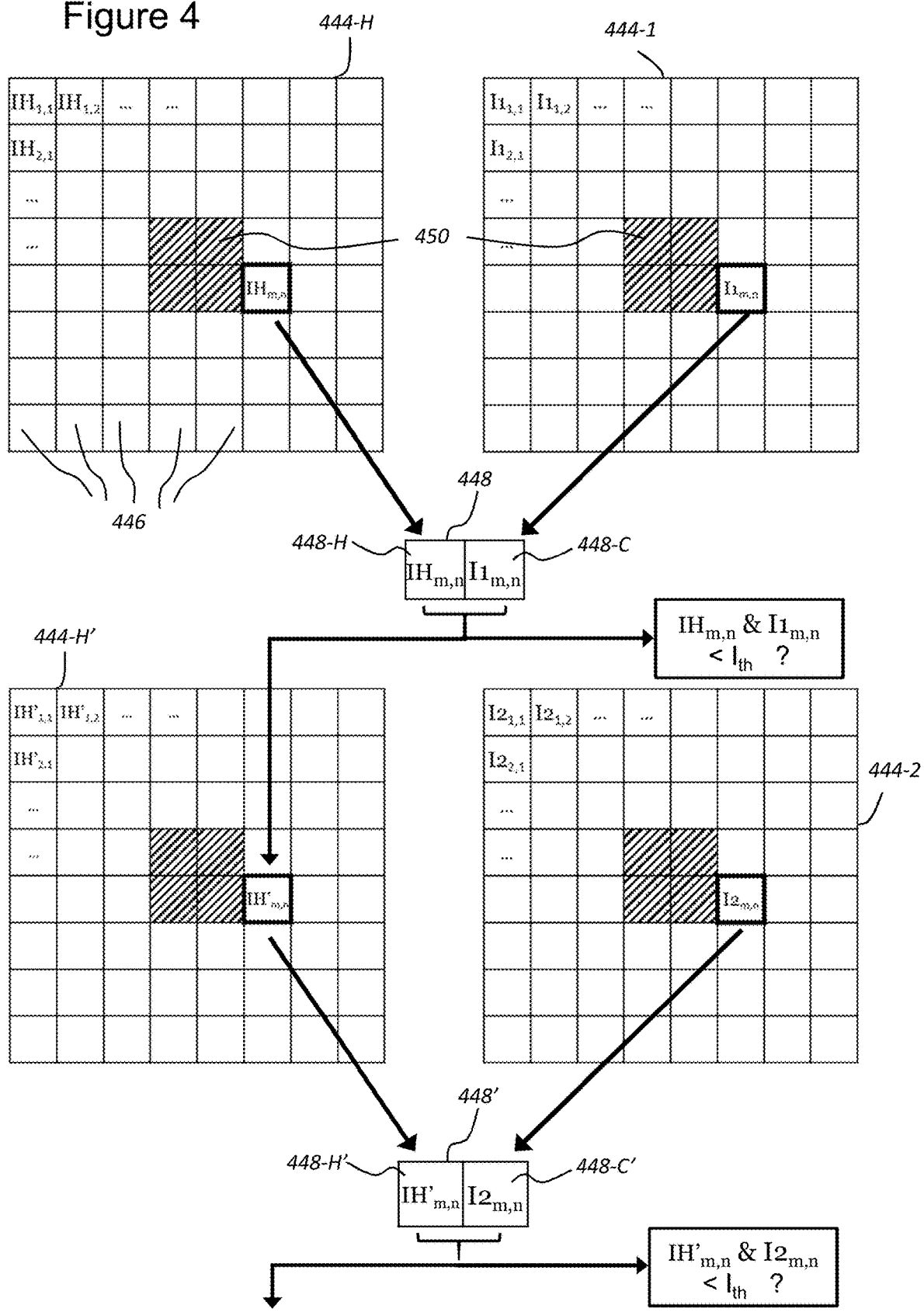

EYE-TRACKING SYSTEM AND METHOD FOR PUPIL DETECTION, ASSOCIATED SYSTEMS AND COMPUTER PROGRAMS

TECHNICAL FIELD

The present disclosure generally relates to the field of eye tracking. In particular, the present disclosure relates to systems and methods for use in pupil detection in eye images for use in an eye-tracking system.

BACKGROUND

In eye tracking applications, digital images are retrieved of the eyes of a user and the digital images are analysed in order to estimate the gaze direction of the user. The estimation of the gaze direction may be based on computer-based image analysis of features of the imaged eye. Many eye-tracking systems estimate gaze direction based on identification of a pupil position, sometimes together with glints or corneal reflections. Therefore, accuracy in the estimation of gaze direction may depend upon an accuracy of the identification or detection of the pupil position and/or the corneal reflections. One or more spurious image features such as stray reflections may be present in the digital images which can detrimentally affect eye feature identification.

One known example method of eye tracking includes the use of infrared light and an image sensor. The infrared light is directed towards the pupil of a user and the reflection of the light is captured by an image sensor.

Portable or wearable eye tracking devices have also been previously described. One such eye-tracking system is described in U.S. Pat. No. 9,041,787 (which is hereby incorporated by reference in its entirety). A wearable eye tracking device is described using illuminators and image sensors for determining gaze direction. The processing power of hardware in a portable of wearable eye tracking device can be limited relative to a free-standing or remote system.

SUMMARY

According to a first aspect of the invention, there is provided an eye-tracking system for excluding pixel locations from a pupil-detection process, the eye-tracking system configured to:
receive image-data comprising a plurality of pixel-arrays, each pixel-array having a plurality of pixel locations and an intensity-value at each of the pixel locations;
for each pixel location of a region of pixel locations:
define an intensity-value-set comprising the intensity-values at the pixel location for two or more of the plurality of pixel-arrays; and
determine the pixel location to be an excluded pixel location if the intensity-value-set does not satisfy an intensity condition; and
exclude the excluded pixel locations from the pupil-detection process.

Such an eye-tracking system can determine excluded pixel locations corresponding to spurious image features and/or regions of static intensity and advantageously provide a candidate map that excludes such pixel locations prior to the pupil-detection process. This pre-processing step can reduce unnecessary processing of pixel locations which have close to zero probability of corresponding to the pupil. Providing the candidate map of pixel locations can also reduce the risk of an erroneous or false pupil detection arising from one or more of the spurious features. In this way, the accuracy of the pupil-detection process and any subsequent eye-gaze tracking is increased.

The plurality of pixel-arrays may comprise one or more image-pixel-arrays, each representing an image of an eye of a user. The eye-tracking system may be further configured to perform the pupil-detection process for one or more of the image-pixel-arrays or one or more corresponding images of the eye of the user.

The eye-tracking system may be further configured to:
for each pixel location of the region of pixel locations, determine the pixel location to be a candidate pixel location if the intensity-value-set satisfies the intensity condition; and
include one or more of the candidate pixel locations in the pupil-detection process.

The plurality of pixel-arrays may include a historical-pixel-array and one or more image-pixel-arrays, wherein the one or more image-pixel-arrays each represent an image of an eye of a user. For each pixel location in the region of pixel locations:
the intensity-value-set may comprise a historical-intensity-value and a current-image-intensity-value, wherein for a first image-pixel-array of the one or more image-pixel-arrays, the eye-tracking system may be configured to:
set the historical-intensity-value to the intensity-value of the pixel location in the historical-pixel-array;
set the current-image-intensity-value to the intensity-value of the pixel location in the first image-pixel-array; and
determine the pixel location as an excluded pixel location if the historical-intensity-value and the current-image-intensity-value of the intensity-value-set are less than an intensity threshold.

Relatively low intensity-values may correspond to pixel locations with lower brightness i.e. darker. Relatively high intensity-values can correspond to pixel locations with higher brightness.

The eye-tracking system may be further configured to exclude the excluded pixel locations from the pupil-detection process and perform the pupil-detection process for the first image-pixel-array or a corresponding first image of the eye of the user.

The eye-tracking system may be further configured to:
for each pixel location of the region of pixel locations, determine the pixel location to be a candidate pixel location if the historical-intensity-value and the current-image-intensity-value of the intensity-value-set are greater than or equal to the intensity threshold; and
include one or more of the candidate pixel locations in the pupil-detection process.

For a second image-pixel-array of the one or more image-pixel-arrays, the eye-tracking system may be further configured to:
for each pixel location in the region of pixel locations:
calculate an updated intensity-value of the pixel location in the historical-pixel-array as the greater of the historical-intensity-value and the current-image-intensity-value;
set the historical-intensity-value of the intensity-value-set to the updated intensity-value;
set the current-image-intensity-value of the intensity-value-set to the intensity-value of the pixel location in the second image-pixel-array; and
determine the pixel location to be an excluded position if the historical-intensity-value and the current-image-intensity-value of the intensity-value-set are less than the intensity threshold. The eye-tracking system may be further configured to repeat this process for subsequent image-pixel-arrays.

The eye-tracking system may be further configured to exclude the excluded pixel locations from the pupil-detection process and perform the pupil-detection process for the second image-pixel-array or a corresponding second image of the eye of the user.

The eye-tracking system may be further configured to:
for each pixel location of the region of pixel locations, determine the pixel location to be a candidate pixel location if the historical-intensity-value and the current-image-intensity-value of the intensity-value-set are greater than or equal to the intensity threshold; and
include one or more of the candidate pixel locations in the pupil-detection process.

The eye-tracking system may be configured to adjust the updated-intensity-value by a slippage-constant prior to setting the historical-intensity-value. The slippage-constant can be a value between 0 and 1.

The plurality of pixel-arrays may comprise a plurality of image-pixel-arrays, each representing an image of an eye of a user. The intensity-value-set for each pixel location may comprise the intensity-values at the pixel location for each of the plurality of image-pixel-arrays. The intensity condition may comprise a condition that at least one intensity-value of the intensity-value-set exceeds an intensity threshold.

The plurality of pixel-arrays may comprise a plurality of image-pixel-arrays, each representing an image of an eye of a user. The intensity-value-set for each pixel location may comprise the intensity-values at the pixel location for each of the plurality of image-pixel-arrays. The intensity condition may comprise a condition that the intensity-value-set comprises a variation in intensity-value. The condition may further comprise that the variation in intensity-value exceeds a variation threshold.

The intensity condition may exclude pixel locations that have a substantially constant intensity-value for each of the plurality of pixel-arrays.

The region of pixel locations may comprise pixel locations outside a safe region of a pixel-array. The safe region may comprise a group of pixel locations in the centre of each pixel-array.

The eye-tracking system may be further configured to:
set a first size and/or a first position of the safe region for a first group of image-pixel-arrays; and
set a second size and/or second position of the safe region for a second group of image-pixel-arrays,
wherein each image-pixel-array represents an image of an eye of a user.

The region of pixel locations may comprise all pixel locations.

The pupil-detection process may comprise a sliding-window based algorithm or a regressor based algorithm.

According to a second aspect, there is provided a head-mounted device comprising any eye-tracking system disclosed herein.

The head-mounted device may comprise a display capable of presenting graphics to a user. The head-mounted device may comprise an extended reality (XR) device. The display may be transparent, for example in an augmented reality (AR) device. The display may be non-transparent, for example in a virtual reality (VR) device. In other examples, the head-mounted device may not comprise a display, for example in glasses for eye-tracking.

According to a further aspect, there is provided a method for excluding pixel locations from a pupil-detection process, the method comprising:
receiving image data comprising a plurality of pixel-arrays, each pixel-array having a plurality of pixel locations and an intensity-value at each of the pixel locations;
for each pixel location of a region of pixel locations:
defining an intensity-value-set comprising the intensity-values at the pixel location for two or more of the plurality of pixel-arrays; and
determining the pixel location to be an excluded pixel location if the intensity-value-set does not satisfy an intensity condition; and
excluding the excluded pixel locations from the pupil-detection process.

There may be provided a computer program, which when run on a computer, causes the computer to configure any apparatus, including a circuit, controller, converter, or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

The computer program may be provided on a computer readable medium, which may be a physical computer readable medium such as a disc or a memory device, or may be embodied as a transient signal. Such a transient signal may be a network download, including an internet download. There may be provided one or more non-transitory computer-readable storage media storing computer-executable instructions that, when executed by a computing system, causes the computing system to perform any method disclosed herein.

BRIEF DESCRIPTION OF THE DRAWINGS

There now follows, by way of example only, a detailed description of embodiments of the invention with reference to the following figures, in which:

FIG. 4 shows a schematic of information flow for an eye-tracking system implementing a historical intensity condition according to an embodiment of the present disclosure;

All the figures are schematic and generally only show parts which are necessary in order to elucidate the respective embodiments, whereas other parts may be omitted or merely suggested.

DETAILED DESCRIPTION

Figure 1:
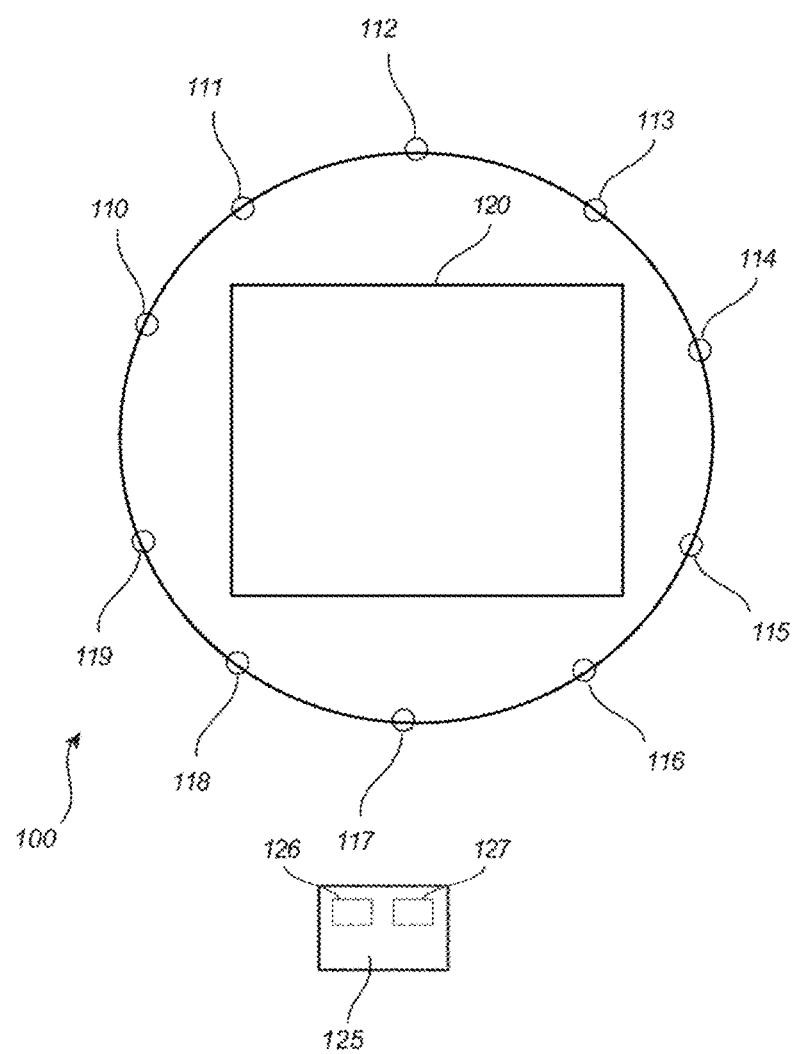
FIG. 1 shows a schematic view of an eye-tracking system which may be used to capture a sequence of images which may be used by example embodiments.

FIG. 1 shows a simplified view of an eye-tracking system 100 (which may also be referred to as a gaze tracking system) in a head mounted device in the form of a virtual or augmented reality (VR or AR) device or VR or AR glasses. The system 100 comprises an image sensor 120 (e.g. a camera) for capturing images of the eyes of the user. The system may optionally include one or more illuminators 110-119 for illuminating the eyes of a user, which may for example be light emitting diodes emitting light in the infrared frequency band, or in the near infrared frequency band and which may be physically arranged in a variety of configurations. The image sensor 120 may for example be an image sensor of any type, such as a complementary metal oxide semiconductor (CMOS) image sensor or a charged coupled device (CCD) image sensor. The image sensor may consist of an integrated circuit containing an array of pixel sensors, each pixel containing a photodetector and an active amplifier. The image sensor may be capable of converting light into digital signals. In one or more examples, it could be an Infrared image sensor or IR image sensor, an RGB sensor, an RGBW sensor or an RGB or RGBW sensor with IR filter.

The eye-tracking system 100 may comprise circuitry or one or more controllers 125, for example including a receiver 126 and processing circuitry 127, for receiving and processing the images captured by the image sensor 120. The circuitry 125 may for example be connected to the image sensor 120 and the optional one or more illuminators 110-119 via a wired or a wireless connection and be co-located with the image sensor 120 and the one or more illuminators 110-119 or located at a distance, e.g. in a different device. In another example, the circuitry 125 may be provided in one or more stacked layers below the light sensitive surface of the light sensor 120.

The eye-tracking system 100 may include a display (not shown) for presenting information and/or visual stimuli to the user. The display may comprise a VR display which presents imagery and substantially blocks the user's view of the real-world or an AR display which presents imagery that is to be perceived as overlaid over the user's view of the real-world.

The location of the image sensor 120 for one eye in such a system 100 is generally away from the line of sight for the user in order not to obscure the display for that eye. This configuration may be, for example, enabled by means of so-called hot mirrors which reflect a portion of the light and allows the rest of the light to pass, e.g. infrared light is reflected, and visible light is allowed to pass. However, other solutions are applicable, such as using diffractive optical elements, DOE, such that the image sensor 120 and/or illuminators 110-119 can be positioned arbitrary in the head mounted device and still be able to capture (or illuminate) an eye of the user.

While in the above example the images of the user's eye are captured by an image sensor 120 comprised in the head mounted device, due to it forming part of the eye-tracking system 100, the images may alternatively be captured by an image sensor separate from an eye-tracking system 100 wherein said image sensor 120 may be comprised in the head mounted device or not.

Figure 2A:
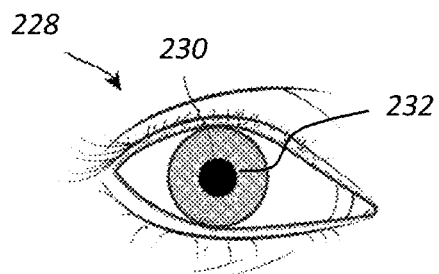
FIG. 2A shows a simplified example image of an eye.

FIG. 2A shows a simplified example of an image of an eye 228, captured by an eye-tracking system such as the system of FIG. 1. A controller of the system may employ image processing (such as digital image processing) for extracting features in the image. The controller may for example identify the location of the pupil 230 in the one or more images captured by the image sensor. The controller may determine the location of the pupil 230 using a pupil-detection process. The controller may also identify corneal reflections 232 in the image of the eye. The controller may estimate a corneal centre based on the corneal reflections 232.

Figure 2B:
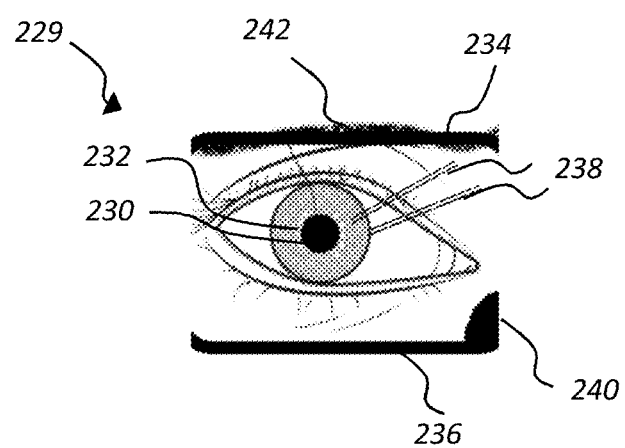
FIG. 2B shows a further simplified example image of an eye.

FIG. 2B shows a further simplified example of an image of an eye 229, captured by an eye-tracking system such as the system of FIG. 1. In this example, the image 229 comprises spurious features that can detrimentally affect identification of the pupil 230 leading to an inaccurate determination of gaze direction. The spurious features in this example include: an upper portion 234 of a frame of spectacles; a lower portion 236 of the frame; stray reflections 238 from a lens of the spectacles; a nose piece 240 (which could be from the spectacles or a head mounted device); and an eyebrow 242. Other examples of spurious image features include mascara, tattoos, freckles, shadows etc.

One or more spurious image features may detrimentally affect an estimation of gaze direction. For example, the controller may erroneously identify a dark region such as the nose piece 240 as a pupil.

In a head mounted system, in particular, the position of the spurious features in a sequence of images image 229 may remain fixed even as a user moves their head and/or eyes. One or more other regions of the sequence of images, such as a user's cheek or forehead, may also remain substantially static and maintain a substantially constant intensity-value or brightness value. In contrast, the pupil position will change in the sequence of images as the user changes their gaze direction. As a result, pixel locations corresponding to the pupil in a particular image will vary in intensity over the plurality of images as the pupil moves to other pixel locations.

Figure 3A:
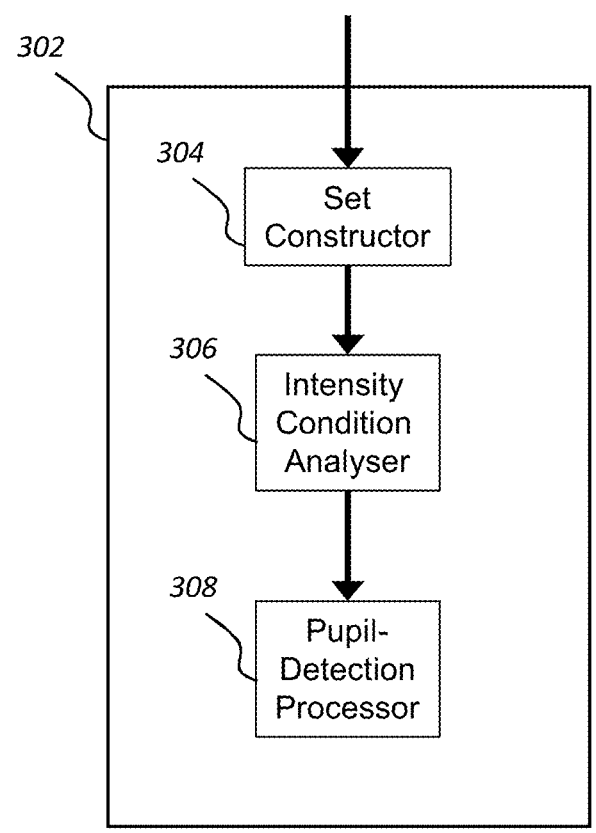
FIG. 3A shows an example of an eye-tracking system according to an embodiment of the present disclosure.

FIG. 3A shows an example of an eye-tracking system 302 according to an embodiment of the present disclosure. The functionality that is illustrated in FIG. 3A may be provided by one or more controllers. The eye-tracking system may be part of, or associated with, a head-mounted device or a remote system. The eye-tracking system may be provided for performing a pupil-detection process on one or more images of an eye of a user. The system can advantageously exclude image pixel locations that correspond to spurious features and/or static regions from the pupil-detection process. As a result, a more accurate pupil-detection process and subsequent eye gaze tracking can be realised. It will be appreciated that the various modules of the eye-tracking system 302 that are described below may be embodied in software or hardware.

The eye-tracking system 302 receives image-data comprising a plurality of pixel-arrays. The plurality of pixel-arrays may comprise one or more image-pixel-arrays, each representing or corresponding to an image of an eye of a user. In some examples, the eye-tracking-system 302 may generate each image-pixel-array from the corresponding image of the eye, which may be received from the image sensor 120. In other examples, each image-pixel-array may comprise the corresponding image of the eye. In some examples, the image-pixel-array may comprise an image signal received directly from the image sensor 120 without any intermediate processing. In the discussion of the embodiments and examples below, the term image-pixel-array(s) may be interchangeably referred to as image(s) (of the eye of the user) depending on context and without loss of meaning.

As discussed below in relation to FIG. 4, the plurality of pixel-arrays may comprise a historical-pixel-array that can track a maximum historical intensity of the one or more image-pixel-arrays.

Each pixel-array has a plurality of pixel locations and an intensity-value at each of the pixel locations. In some examples, the pixel-array may comprise a two-dimensional array of pixel locations. The two-dimensional array may be a square array, for example a 50×50, 100×100 or 200×200 array of pixel locations. In other examples, the pixel-array may be a rectangular array. Each pixel location may correspond to a pixel of the image sensor 120 of the eye-tracking system 100, 302. In another example, each pixel location corresponds to a group of pixels of the image sensor 120 of the eye-tracking system 100, 302. Alternatively, a pixel location may be a location in a two-dimensional array that corresponds to a down-sampled or cropped image from the image sensor 120.

The intensity-value at a pixel location may be a digital representation of an intensity of light incident at a corresponding pixel of the image sensor 120. For example, the intensity-value may be an 8-bit digital value.

Figure 3B:
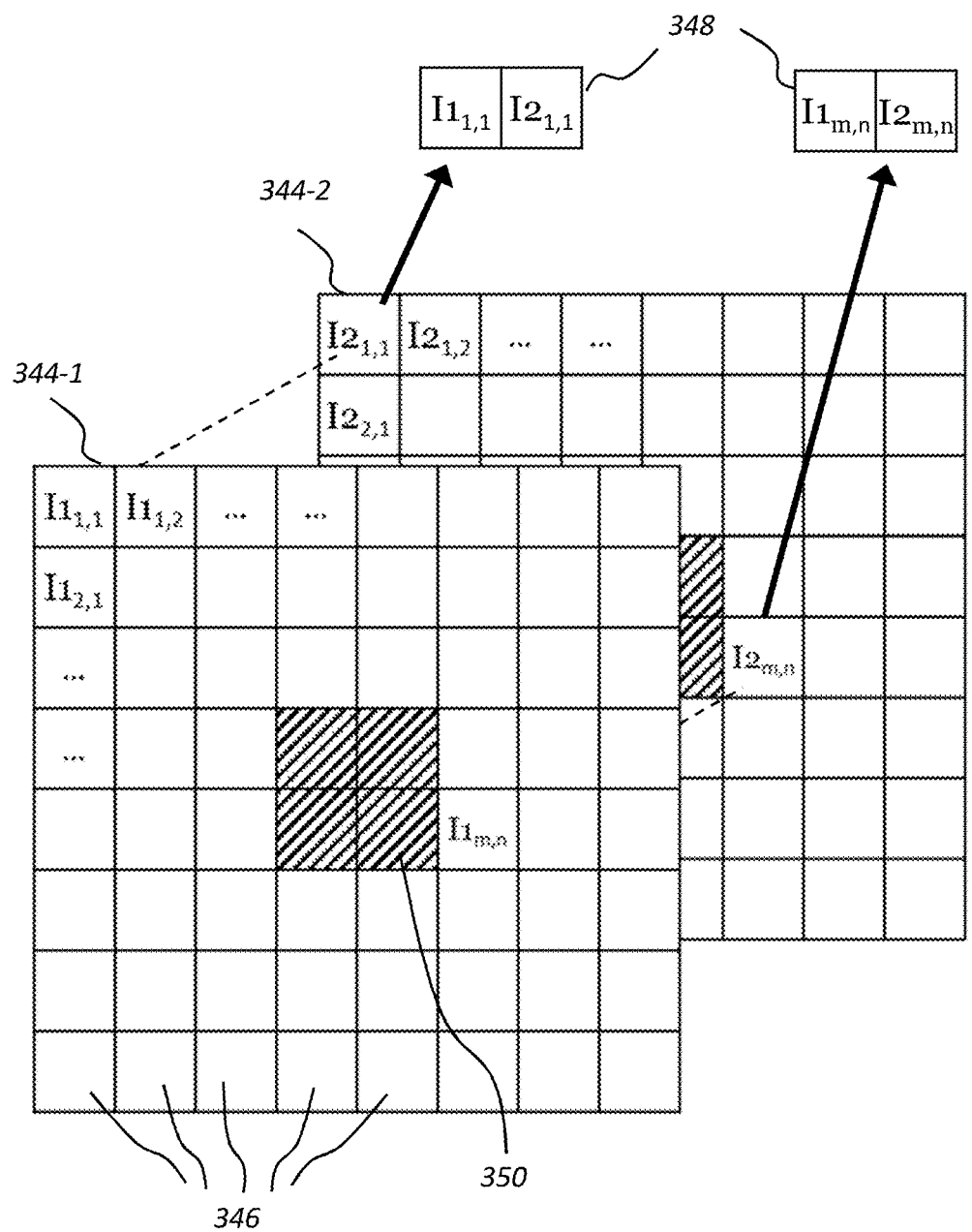
FIG. 3B shows an example schematic of pixel-arrays and associated intensity-value-sets.

FIG. 3B shows a schematic of two pixel-arrays 344-1, 344-2. Each pixel-array 344-1, 344-2 may be an image-pixel-array such that it corresponds to an image of the eye of the user. Each pixel-array 344-1, 344-2, comprises a plurality of pixel locations 346. Each pixel location 346 has an intensity-value, $IX_{m,n}$, wherein X denotes an array number and m,n denote the pixel location or co-ordinates within the pixel-array 344-1, 344-2.

The eye-tracking system 302 includes a set constructor 304 that defines an intensity-value-set 348 for each pixel location 346 of a region of pixel locations. For each pixel location (m,n) 346, the intensity-value-set 348 comprises the intensity-values, $IX_{m,n}$, at the pixel location (m,n) for two or more of the plurality of pixel-arrays 344-1, 344-2. In this example, the intensity-value-set 348 of each pixel location 346 comprises the intensity-values, $I1_{m,n}$, $I2_{m,n}$, for each of the two pixel-arrays 344-1, 344-2.

The region of pixel locations defines pixel locations 346 for the eye-tracking system 302 to analyse to determine if they comprise spurious image features or static regions and can therefore be excluded from a pupil-detection process. In some examples, the region of pixel locations may comprise all pixel locations 346 in the pixel-array 344-1, 344-2. In other examples the region of pixel locations may comprise pixel locations outside a safe-region 350. The safe region 350 may define pixel locations 346 that cannot be excluded from the pupil-detection process. The safe-region 350 may correspond to a central region of each pixel-array 344-1, 344-2. The safe region can define a group of pixel locations in which a pupil is most likely to be found and that the eye-tracking system will therefore always include in a pupil-detection-process.

The eye-tracking system 302 further includes an intensity condition analyser 306 that receives each intensity-value-set 348, corresponding to each pixel location 346 in the region of pixel locations, from the set constructor 304. For each intensity-value-set 348, the intensity condition analyser 306 determines the corresponding pixel location 346 to be an excluded pixel location if the intensity-value-set 348 does not satisfy an intensity condition. In this way, intensity-values from corresponding pixel locations across two or more of the plurality of pixel-arrays are processed to determine whether or not that pixel location 346 should be excluded from a subsequent pupil-detection process. Example intensity conditions are discussed below and may comprise a historical intensity condition, an intensity threshold condition or a variation threshold condition.

A pupil-detection processor 308 receives information relating to the excluded pixel locations from the intensity condition analyser 306. The pupil-detection processor 308 excludes the excluded pixel locations from the pupil-detection process. The pupil-detection processor 308 may then perform the pupil-detection process for at least one of the plurality of pixel-arrays 344-1, 344-2.

In one or more examples, the plurality of pixel-arrays 344-1, 344-2 comprises one or more image-pixel-arrays and the pupil-detection-processor may perform the pupil-detection process on one or more of the image-pixel-arrays or the one or more corresponding images of the eye of the user.

In one or more examples, the intensity condition analyser 306 may be further configured, for each pixel location 346 in the region of pixel locations, to determine the pixel location 346 to be a candidate pixel location if the corresponding intensity-value-set 348 does satisfy the intensity condition. The pupil-detection processor 308 may then include the candidate pixel locations in the pupil-detection process.

The pupil-detection process may comprise a known pupil-detection process. For example, the pupil-detection processor 308 may implement a pupil-detection process comprising a sliding window classifier algorithm in which it moves a centre of a pixel-window sequentially over different pixel locations 346 in the pixel-array 344-1, 344-2. The pupil-detection processor 308 may then analyse the intensity-values of pixel locations 346 within the pixel window to determine a probability that the pixel location 346 corresponding to the centre of the pixel-window is a pupil centre.

The pupil-detection processor 308 may exclude the excluded pixel locations from a sliding window classifier pupil-detection process by excluding centring the pixel-window on the excluded pixel locations. In addition, or alternatively, the pupil-detection processor 308 may exclude any excluded pixel locations that lie within the pixel-window from analysis.

The eye-tracking system 302 can be considered as performing two main steps prior to the pupil-detection process: (i) detect regions of static intensity, particularly low intensity, in the eye images; and (ii) exclude these regions from the pupil-detection process. The eye-tracking system 302 may generate a candidate-map of pixel locations to be processed by the pupil-detection process. The eye-tracking system 302 may exclude the excluded pixel locations from the candidate-map prior to the pupil-detection process. The eye-tracking system 302 will then not perform the pupil-detection process on these excluded pixel locations.

In some examples, the eye-tracking system 302 may determine further excluded pixel locations based on, for example, their proximity to the edge of the image sensor, correspondence to known dead pixels in the image sensor and/or detection of other non-pupil features in the plurality of images. The pupil-detection processor 308 may exclude these further excluded pixel locations from the candidate-map and/or the pupil-detection process.

By determining excluded pixel locations corresponding to spurious image features and/or regions of static intensity, the eye-tracking system 302 can advantageously provide a candidate map of pixel locations that excludes regions corresponding to spurious image features and/or static intensity prior to the pupil-detection process. This pre-processing step can reduce unnecessary processing of pixel locations which have close to zero probability of corresponding to the pupil. Providing the candidate map of pixel locations can reduce the risk of an erroneous or false pupil detection arising from one or more of the spurious features. In this way, the accuracy of the pupil-detection process and any subsequent eye-gaze tracking is increased. In addition, by excluding some pixel locations from the pupil-detection process, the computational load and resulting processing time in performing the pupil-detection process is reduced (fewer potential pupils are processed within the pupil-detection algorithm). The reduced computational load can result in faster processing times and/or a enable the use of a more powerful pupil-detection algorithm leading to further improvements in accuracy. The reduced computational load can be particularly advantageous in devices with limited hardware resources. In some examples, computation performance may be improved by approximately 10%. In some examples, pupil-detection and eye tracking may not function correctly without an example eye-tracking system as disclosed herein.

It will be appreciated that the disclosed systems and methods are not limited to a head mounted device. They may also be applied in remote eye-tracking systems with a fixed camera or image sensor. In such systems, spurious image features such as static dark regions may arise from shadows, obstructing objects in the near field and or stray reflections. These features may remain static even as a user moves relative to the image sensor.

FIG. 4 shows a schematic of information flow for an eye-tracking system implementing a historical intensity condition according to one or more embodiments of the invention.

In this example, the plurality of pixel-arrays comprises a historical-pixel-array 444-H and one or more image-pixel-arrays 444-1, 444-2, each image-pixel-array 444-1, 444-2 representing an image of an eye of a user. The historical-pixel-array 444-H is a reference-array that tracks the brightest historical intensity-value at each pixel location 446. In the following description of FIG. 4, the image-pixel-arrays 444-1, 444-2 may sometimes be referred to as the images 444-1, 444-2 (of the eye of the user), without loss of meaning.

The eye-tracking system may initialise the historical-pixel-array 444-H, for example by setting the intensity-value, $IH_{m,n}$, of each pixel location 446 to zero. In other examples, the eye-tracking system may receive the historical-pixel-array 444-H from a memory in which the eye-tracking system had previously stored the historical-pixel-array 444-H following the processing of one or more previous images of the eye of the user.

In examples implementing the historical intensity condition, the intensity-value-set 448 for each pixel location 446 comprises two intensity-values: (i) a historical-intensity-value 448-H; and (ii) a current-image-intensity-value 448-C.

For a first image-pixel-array 444-1, corresponding to a first image of the eye of the user, the set constructor 304 of the eye-tracking system 100, 302 sets the historical-intensity-value 448-H and the current-image-intensity-value 448-C in the intensity-value-sets 448. For a particular intensity-value-set 448, the set constructor 304 sets the historical-intensity-value 448-H to the intensity-value, $IH_{m,n}$, of the corresponding pixel location 446 in the historical-pixel-array 444-H. The set constructor 304 also sets the current-image-intensity-value 448-C to the intensity-value, $I_{1_{m,n}}$, of the corresponding pixel location 446 in the first image-pixel-array 444-1. The set-constructor 304 carries out this process for the intensity-value-sets 448 corresponding to each pixel location 446 in the region of pixel locations.

After the set constructor 304 sets the intensity-values 448-H, 448-C in the intensity-value-set 448, the intensity condition analyser 306 of the eye-tracking system 100, 302 can determine if the intensity-value-set 448 satisfies the historical intensity condition. To achieve this, the intensity condition analyser 306 may compare each of the historical-intensity-value 448-H and the current-image-intensity-value 448-C to an intensity threshold, $I_{th}$. The intensity condition analyser 306 may determine the pixel location to be an excluded pixel location if both the historical-intensity-value 448-H and the current-image-intensity-value 448-C of the intensity-value-set 448 are less than the intensity threshold, $I_{th}$. The intensity condition analyser 306 may also determine the pixel location to be a candidate pixel location if either the historical-intensity-value 448-H or the current-image-intensity-value 448-C of the intensity-value-set 448 are greater than or equal to the intensity threshold, $I_{th}$, that is they satisfy the historical intensity condition. The intensity condition analyser 306 can carry out this process for the intensity-value-sets 448 corresponding to each pixel location 446 in the region of pixel locations. By determining pixel locations to be excluded pixel locations or candidate pixel locations, the intensity condition analyser 306 may determine a candidate-map of pixel locations for the pupil-detection process.

Once the intensity condition analyser 306 has processed all intensity-value-sets 484 for the first image-pixel-array 444-1, the pupil-detection processor 308 of the eye-tracking system 100, 302 may exclude the excluded pixel locations from the pupil-detection process. The pupil-detection processor 308 may also include the candidate pixel locations in the pupil-detection process. In other words, the pupil-detection processor 308 may include or exclude pixel locations for the pupil-detection process according to the candidate-map. The pupil-detection processor 308 may then perform the pupil-detection process on the first image/first image-pixel-array 444-1. In other examples, the eye-tracking system may continue to set intensity-value-sets 448 and determine excluded pixel locations and/or candidate pixel locations for subsequent images of the eye of the user. The pupil-detection processor 308 may then exclude or include pixel locations for the pupil-detection process and perform the pupil-detection process on one or more images of the eye of the user.

After the eye-tracking system has determined if a particular pixel location 446 is an excluded pixel location, the eye-tracking system may calculate an updated intensity-value, of the pixel location 446 in the historical-pixel-array 444-H'. The updated intensity-value, may comprise the greater of the historical-intensity-value 448-H and the current-image-intensity-value 448-C in the intensity-value-set 448. In this way, the eye-tracking system updates the historical-pixel-array 444-H' such that it tracks or stores a maximum historical intensity-value at each pixel location 446. The eye-tracking system may carry out this process for the intensity-value-sets corresponding to each pixel location 446 in the region of pixel locations. In some examples, the updated historical-pixel-array 444-H' can define the candidate-map of pixel locations.

The eye-tracking system may then continue to process a second image-pixel-array 444-2/second image of the eye of the user. The set constructor 304 may set the historical-intensity-value 448-H' and the current-image-intensity-value 448-C' in the intensity-value-sets 448'. For a particular intensity-value-set 448', the set constructor 304 sets the historical-intensity-value 448-H' to the updated intensity-value, $IH'_{m,n}$, at the corresponding pixel location 446 in the historical-pixel-array 444-H'. The set constructor 304 also sets the current-image-intensity-value 448-C' to the intensity-value, $I_{2_{m,n}}$, at the corresponding pixel location 446 in the second image-pixel-array 444-2. The set-constructor carries out this process for the intensity-value-sets 448 corresponding to each pixel location 446 in the region of pixel locations.

The intensity condition analyser 306 may then assess the new values in each intensity-value-set against the intensity threshold in the same way as described above in relation to the first image. In this way, the intensity condition analyser 306 may determine each pixel location in the region of pixel locations as a candidate pixel location or an excluded intensity location. In other words, the intensity condition analyser 306 determines an updated candidate-map of pixel locations.

As described above in relation to the first image 444-1, the pupil-detection processor 308 may then exclude or include pixel locations in the pupil-detection process and optionally perform the pupil-detection process for the second image 444-2. By updating the historical-pixel-array 444-H'/candidate-map and performing the pupil-detection process for each image of the eye of the user, the eye-tracking system determines excluded pixel locations/static dark regions and performs the pupil-detection process one image at a time, which may be referred to as an "on-the-fly" pupil-detection process.

In other examples, the eye-tracking system may continue to update the historical-pixel-array 444-H'/candidate map by processing further subsequent images of the eye of the user and perform the pupil-detection process after a predetermined number of images have been used to determine the candidate-map. In this way, the candidate map is determined from a buffer or batch of images of the user of the eye. This can allow a stable candidate-map to develop that excludes static dark regions of an image with a higher degree of certainty than the on-the-fly method.

As more images of the user's eye are processed, the eye-tracking system determines excluded pixel locations corresponding to static dark regions with greater accuracy because the historical-pixel-array 444-H' indicates pixel locations that have been less than the intensity threshold for a sustained period of time. However, the eye-tracking system can effectively determine excluded pixel locations (and optionally perform the pupil-detection process) after processing the first image-pixel-array 444-1. Even if the user's pupil is within the region of pixel locations to be analysed and therefore the eye-tracking system erroneously excludes the pixel locations corresponding to the dark pupil for the first image, the eye-tracking system will determine the pixel locations as candidate pixel locations as soon as the pupil moves in subsequent images. Therefore, even in this worst-case scenario, accurate pupil-detection can be established after a handful of images. Defining a large safe region 450, particularly for the first image or a first group of images can mitigate this risk of erroneously excluding the pupil location in the first image.

As described above, the region of pixel locations, for which pixel locations 446 may be excluded from the pupil-detection process, may comprise pixel locations 446 outside a safe-region 450. In this way, the safe region 450 may define pixel locations 446 that cannot be excluded from the pupil-detection process. For the first few images of the eye of the user, the degree of uncertainty about which pixel locations correspond to spurious features and which correspond to eye features may be high, particularly if the images are processed on the fly. Therefore, in some examples, the eye-tracking system may define a large safe-region 450 for a first group of images of the eye. For example, the safe region may comprise 10-70%, preferably 20-60% of the pixel locations. As the eye-tracking system determines static dark regions with more certainty and performs the pupil-detection process with greater accuracy, the eye-tracking system may reduce the size of the safe region (increase the region of pixel locations to be assessed for spurious features) for subsequent images. In this way, the eye-tracking system may be arranged to: set a first size and/or first position of the safe region for a first group of images of the eye; and set a second size and/or second position of the safe region for a second group of images of the eye. A group of images may comprise one or more images. The second size may be smaller than the first size. The system may set further sizes and/or positions of the safe region for further groups of images. In this way, the system can adapt the size and or position of the safe region for subsequent images of the eye.

As described above, for head mounted devices in particular, the position of the spurious features in a sequence of images may remain fixed even as a user moves their head and/or eyes. However, if the user's activity level and movement is sufficiently vigorous (for example jumping) the head mounted device may slip or move. As a result, the position of image features may move relative to the image sensor 120. Therefore, in one or more examples, the eye-tracking system may apply slippage compensation when determining the updated intensity-values, $IH'_{m,n}$, in the historical-pixel-array 444-H. The eye-tracking system may adjust the updated-intensity-value by a slippage-constant. The adjustment may comprise multiplication, shifting, subtraction or any other scaling adjustment. In this way, the tracked or stored historical maximum intensity-value, $IH'_{m,n}$ for each pixel location may be attenuated for each subsequent image of an eye of a user. In this way, the stored maximum intensity-values, $IH'_{m,n}$, at pixel locations that correspond to a candidate pixel location prior to a user movement and correspond to a static dark region after the movement can be gradually reduced to less than the intensity threshold and become excluded pixel locations.

In determining the excluded pixel locations for a plurality of images 444-1, 444-2 of the eye of the user according to the historical intensity condition, the eye-tracking system 100, 302 may be considered as being arranged to:
(i) receive the historical-pixel-array 444-H, wherein each intensity-value may represent the historical maximum intensity for that pixel location;
(ii) initialise the historical-pixel-array 444-H, for example by setting all intensity-values to zero;
(iii) optionally define a safe region 450 comprising a portion, for example 10 to 70%, of pixel locations centred on the centre of the pixel-array of the images 444-1, 444-2;
(iv) receive the plurality of images 444-1, 444-2 of the user's eye, for example from the image sensor of the eye-tracking system 100, 302 at times t=1, 2, . . . , N;
(v) for each of the plurality of images 444-1, 444-2:
(a) update the intensity-value of each pixel location in the historical-pixel-array 444-H to the pixel-wise maximum value of the historical-pixel-array and the current image received at a time t;
(b) optionally adjust the updated intensity-values in the historical-pixel-array 444-H with a slippage constant;
(c) exclude pixel locations for which the corresponding intensity-value in the historical-pixel-array 444-H is less than the intensity threshold; and
(d) optionally perform a pupil-detection process on pixel locations that have not been excluded.

Figure 5:
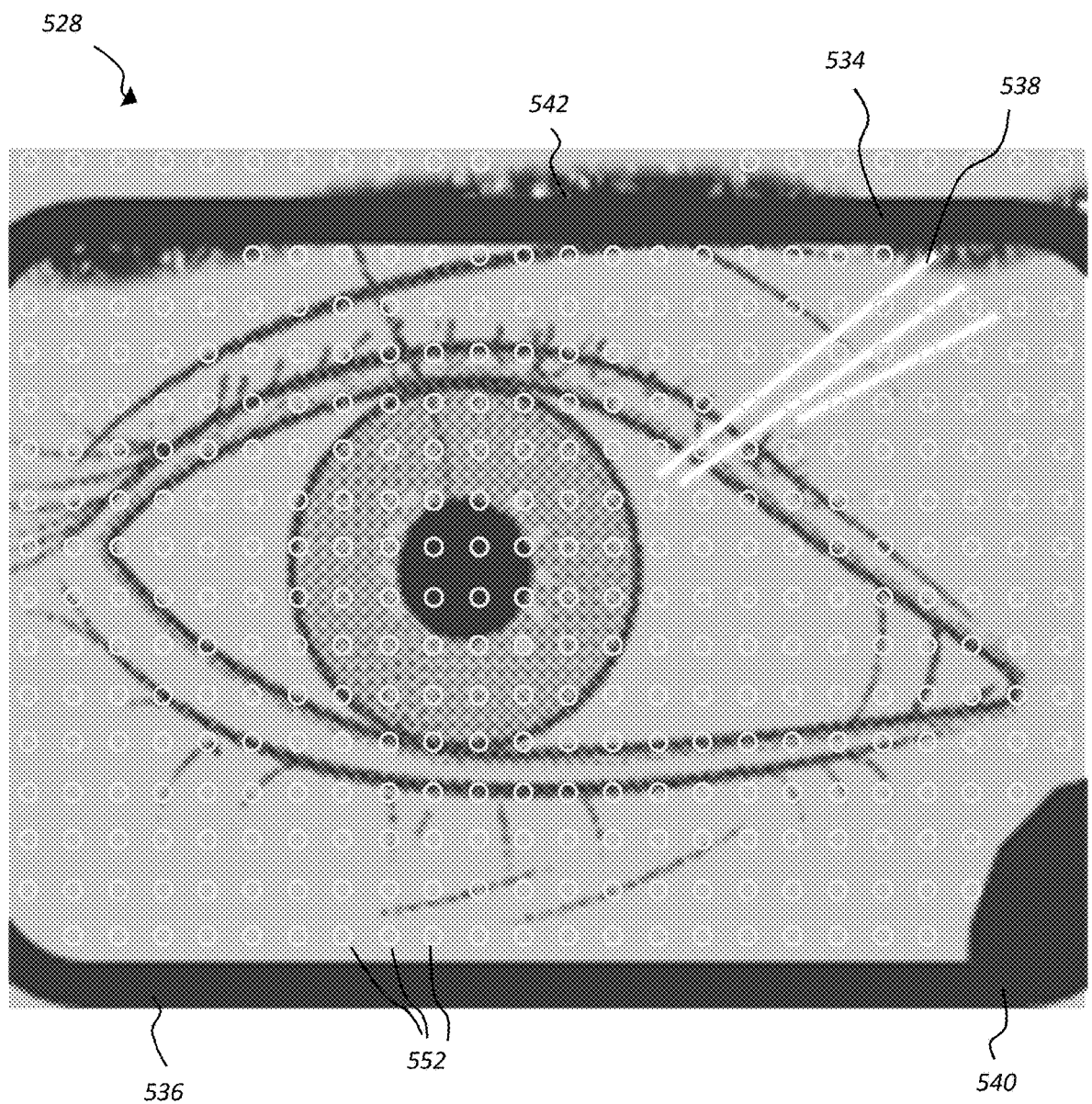
FIG. 5 illustrates an image of an eye for which an eye-tracking system according to an embodiment of the present disclosure has determined excluded pixel locations using a historical intensity condition.

FIG. 5 illustrates an image of an eye 528 for which an eye-tracking system according to an embodiment of the present disclosure has determined excluded pixel locations using the historical intensity condition.

Candidate pixel locations 552 at which the pupil-detection processor performs the pupil-detection process are illustrated as an array of circles on the image. The array of candidate pixel locations 552 define the candidate-map of pixel locations. In this example, the candidate-map of candidate pixel locations 552 is shown after a plurality of images of the user's eye have been processed. In this example, the pupil-detection processor would continue to perform the pupil detection process at the candidate pixel locations 552.

The image 528 illustrates regions of excluded pixel locations corresponding to an upper portion 534 of a spectacle frame, a lower portion 536 of the spectacle frame, a nose piece 540 and an eyebrow 542. These excluded locations are recognisable from FIG. 5 by the absence of the circles that represent candidate pixel locations 552. In other words, they do not form part of the candidate map of pixel locations. The eye-tracking system excludes the excluded pixel locations from the 25×25 array (or 200×200 pixel-array) prior to the pupil-detection process.

In the example of FIG. 5, the intensity condition comprises the historical intensity condition as described in relation to FIG. 4. Pixel locations corresponding to the upper frame portion 534, the lower frame portion 536, nose piece 540 and eyebrow 542 will remain dark throughout the plurality of images (assuming no relative movement of the image sensor and the eye, such as in a head mounted device). That is, they can be considered as static dark areas. The intensity threshold can be set to an intensity-value such that these static dark areas will comprise intensity-values that are all less than the intensity threshold. The intensity threshold may comprise an intensity-value that is sufficiently low to create a contrast relative to surrounding pixel locations in order for the pupil detection algorithm to detect a false pupil.

FIG. 5 also shows stray reflections 538 of an IR illumination source from the lens of the spectacles. However, pixel locations corresponding to the stray reflections 538 have not been excluded because their intensity-values are greater than the intensity threshold. As explained further below in relation to FIG. 6, a variation intensity condition can enable the eye-tracking system to exclude regions of static bright areas, such as stray reflections.

Figure 6:
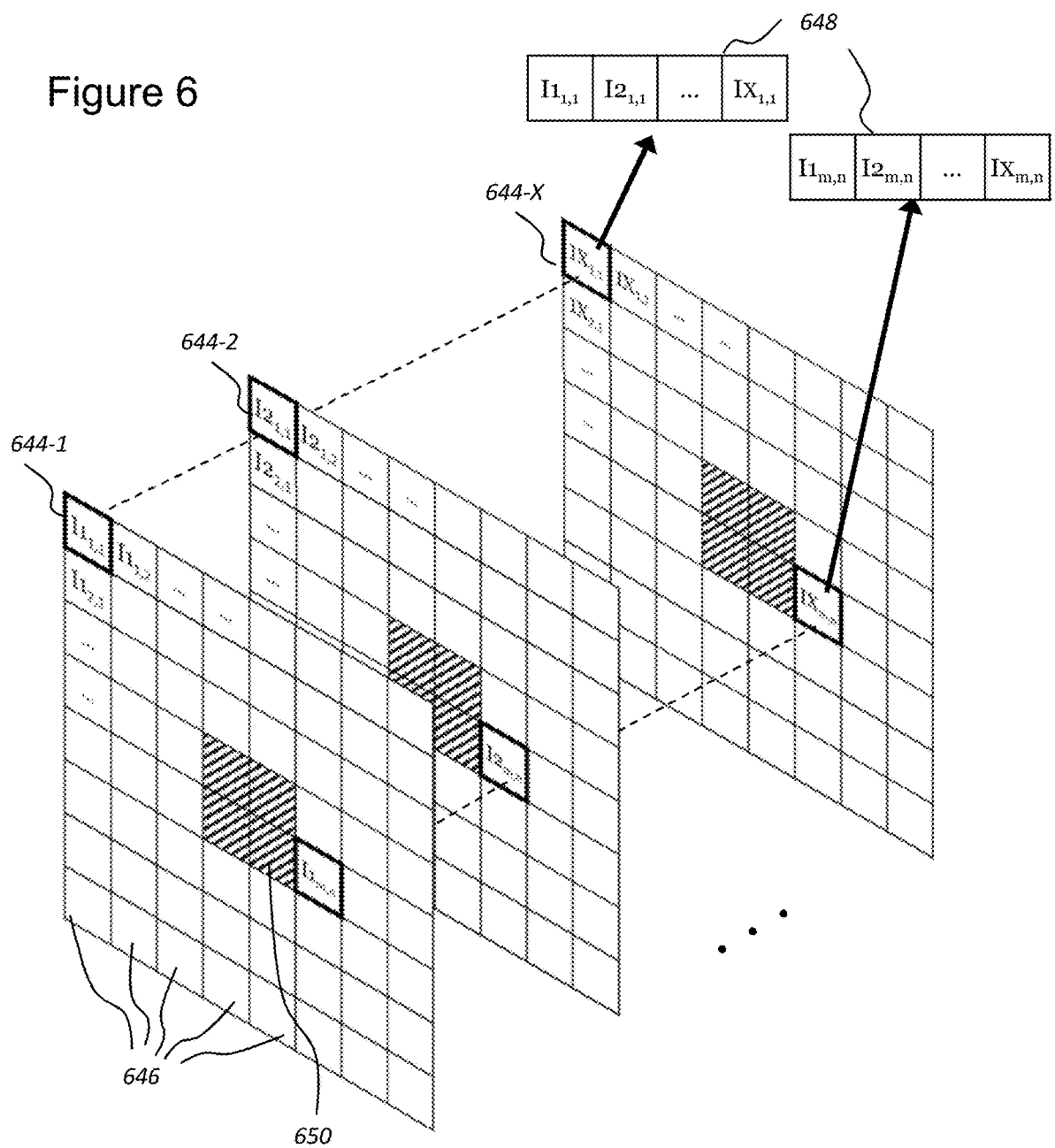
FIG. 6 shows a schematic of a plurality of image-pixel-arrays and corresponding intensity-value-sets for an eye-tracking system implementing an intensity threshold or a variation threshold intensity condition according to embodiments of the present disclosure.

FIG. 6 shows a schematic of a plurality of pixel-arrays 644-1, 644-2, 644-X and corresponding intensity-value-sets 648 for an eye-tracking system implementing an intensity threshold or variation threshold intensity condition according to one or more embodiments of the invention.

In this example, the plurality of pixel-arrays comprises a plurality of image-pixel-arrays 644-1, 644-2, 644-X, each corresponding to an image of an eye of a user. In this example, there is no historical-pixel-array. In the description of FIG. 6, the image-pixel-arrays 644-1, 644-2, 644-X may sometimes be referred to as the images 644-1, 644-2, 644-X (of the eye of the user), without loss of meaning.

For each pixel location 646 in the region of pixel locations, the set constructor 304 may define an intensity-value-set 648 comprising the intensity-values, $IX_{m,n}$, at the pixel location for each of the plurality of images 644-1, 644-2, 644-X. Therefore, the intensity-value-sets 648 comprise the intensity-values, $IX_{m,n}$, at a particular pixel location 646 for a batch or buffer of images 644-1, 644-2, 644-X. As a result, the eye-tracking system 100, 302 may determine excluded pixel locations and/or candidate pixel locations (the candidate-map) based on the buffer of images 644-1, 644-2, 644-X prior to performing the pupil-detection process. In some examples, the eye-tracking system 100, 302 may only determine the candidate-map based on a buffer of a first group of images 644-1, 644-2, 644-X as part of a start-up routine, for instance when an eye-tracking system is first switched on. In other embodiments, the buffer of images 644-1, 644-2, 644-X and the corresponding candidate-map may be continuously updated as the eye-tracking system 100, 302 receives subsequent images of the eye.

Each pixel-array 644-1, 644-2, 644-3 comprises a safe region 650 as described above in relation to FIG. 3 and FIG. 4. The region of pixel locations, for which pixel locations are analysed according to the intensity condition, may comprise pixel locations 646 outside the safe region 650. As described in relation to FIG. 4, the eye-tracking system may adapt the size and/or position of the safe region 650 as it receives further images and updates the buffer of images 644-1, 644-2, 644-X.

The intensity condition analyser 306 may analyse the intensity-value-sets 648 corresponding to the pixel locations 646 to determine excluded pixel locations and/or candidate pixel locations according to one or more intensity conditions.

FIG. 6 shows three example intensity-value-sets 648-1, 648-2, 648-3 defined by the set constructor 304 based on a buffer of 10 images 644-1, 644-2, 644-X. The intensity-values are on a 4-bit scale from 0 to 15.

A first intensity-value-set 648-1 corresponds to a first pixel location, (1,1), in the upper left corner of the images 644-1, 644-2, 644-X. The first pixel location is in an area of static darkness in which the intensity-value is either 1 or 2 on the 4-bit scale. A second intensity-value-set 648-2 corresponds to a second pixel location, (5,5) towards the upper left corner of the images 644-1, 644-2, 644-X. The second pixel location is in an area of static intensity, but not a static dark area. This may correspond to a portion of the user's face surrounding their eye or to a stray reflection. The intensity-value only varies between 9 and 10 on the 4-bit scale. A third intensity-value-set 648-3 corresponds to a third pixel location, (m,n), towards the centre of the images 644-1, 644-2, 644-X. The pupil has traversed the third pixel location twice during the 10 images as can illustrated by the variation in intensity-values. The pupil traversals can be seen in the $3^{rd}/4^{th}/5^{th}$ and $8^{th}/9^{th}$ intensity-values of the third-intensity-value-set 648-3 during which the intensity-value drops from 8 or 9 to 0 or 1. The intensity-values in the third intensity-value-set 648-3 vary between a maximum value of 9 (for images in which the pixel location corresponds to the iris or sclera) and a minimum value of zero (for images in which the pixel location corresponds to the pupil) on the 4-bit scale.

As a first example, the intensity condition analyser 306 may determine the first, second or third pixel locations to be excluded pixel locations if their corresponding intensity-value-sets 648-1, 648-2, 648-3 fail to satisfy an intensity threshold condition. The intensity threshold condition may comprise a condition that at least one intensity-value in the intensity-value-set is greater than or equal to an intensity threshold. For an intensity threshold of 3, the intensity condition analyser 306 may determine: (i) that the second intensity-value-set 648-2 and the third intensity-value-set 648-3 satisfy the intensity threshold condition; and (ii) that the first intensity-value-set 648-1 does not satisfy the intensity threshold condition. Therefore, the intensity condition analyser 306 may determine the first pixel location to be an excluded pixel location. The intensity condition analyser 306 may also determine the second pixel location, corresponding to an area of static intensity, to be a candidate pixel location. As a result, the eye-tracking system may not exclude pixel locations corresponding to spurious bright features, such as stray reflections, from the pupil-detection process when using the intensity threshold condition (see FIG. 5).

Figure 7:
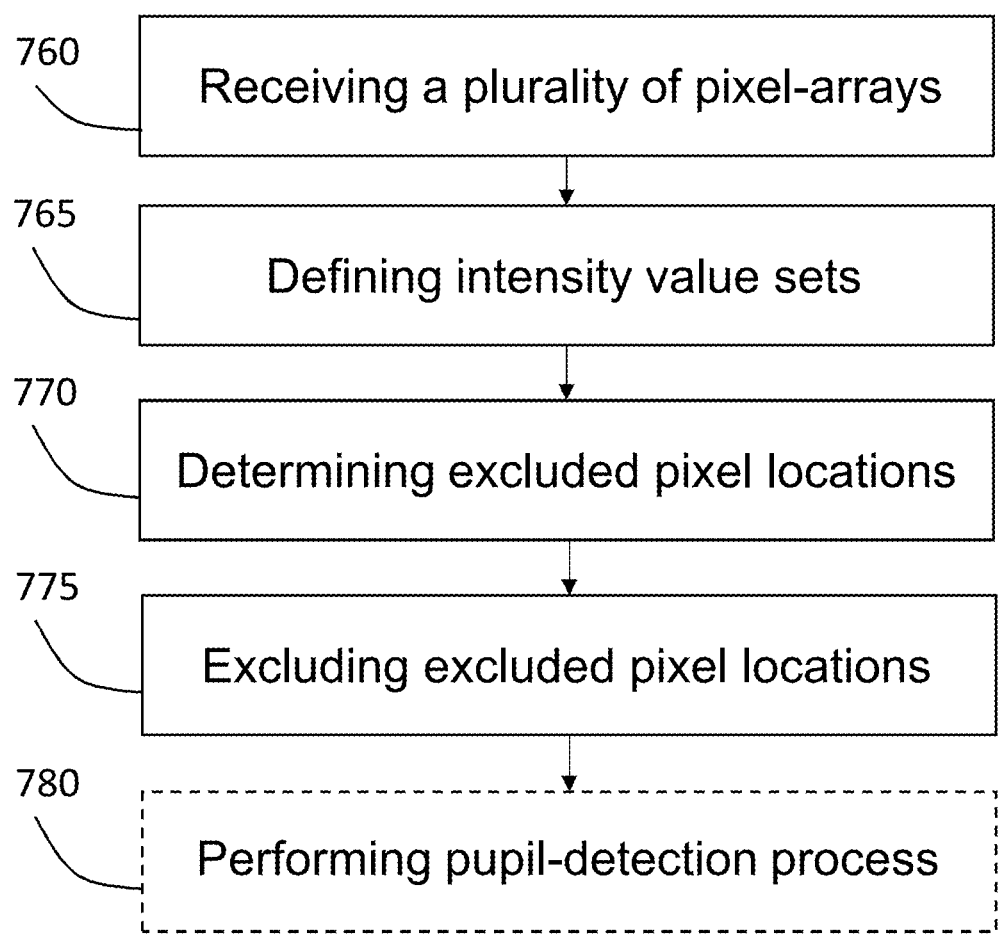
FIG. 7 is a flow chart of an example of a method according to an embodiment of the present disclosure.

As a second example, the intensity condition analyser 306 may determine the first, second or third pixel locations to be excluded pixel locations if their corresponding intensity-value-sets 648-1, 648-2, 648-3 fail to satisfy a variation intensity condition. The variation intensity condition may comprise a condition that the intensity-value-set comprises a variation in intensity-value. The variation may be defined by a variation threshold. The variation may comprise an absolute intensity variation (maximum intensity-value—minimum intensity-value), a standard deviation in intensity-values or some other measure of variance in the intensity-values in a particular intensity-value-set. For an absolute intensity variation of 3, the intensity condition analyser 306 may determine that an intensity-value-set 648-1, 648-2, 648-3 will satisfy the intensity condition if a difference between the maximum intensity-value and the minimum intensity-value in the intensity-value-set 648-1, 648-2, 648-3 is greater than or equal to 3. Therefore, the intensity condition analyser 306 may determine that: (i) the third intensity-value-set 648-3 satisfies the intensity variation condition because the absolute variation is 9; and (ii) the first intensity-value-set 648-1 and the second-intensity-value-set 648-2 do not satisfy the intensity variation condition because they have an absolute variation of 1. Therefore, the intensity condition analyser 306 may determine that the first and second pixel locations are excluded pixel locations based on this intensity variation condition. In this way, the eye-tracking system 100, 302 can exclude areas of static brightness, such as the stray reflections in FIG. 5, from the pupil-detection process using the intensity variation condition FIG. 7 illustrates a process flow of a method that may be performed by the eye-tracking system 100, 302 of according to one or more embodiments of the present disclosure.

The method for pupil detection for eye tracking comprises receiving 760 a plurality of pixel-arrays. Each pixel-array has a plurality of pixel locations and an intensity-value at each of the pixel locations. The method further comprises, for each pixel location in a region of pixel locations: (i) defining 765 an intensity-value-set comprising the intensity-values at the pixel location for two or more of the plurality of pixel-arrays; and (ii) determining 770 the pixel location to be an excluded pixel location if the intensity-value-set does not satisfy an intensity condition. The method further comprises excluding 775 the excluded pixel locations from the pupil-detection process. In one or more examples, the plurality of pixel-arrays may comprise one or more image-pixel-arrays, each representing an image of an eye of a user. The method may optionally comprise performing 780 the pupil-detection process for one or more of the image-pixel-arrays or the corresponding one or more images.

In summary, the present disclosure describes eye-tracking systems and methods that can provide more accurate and more efficient pupil detection by excluding pixel locations corresponding to spurious image features and/or regions of static intensity, particularly dark static regions. Embodiments can be used in eye-tracking systems and methods for improved gaze tracking.

The invention claimed is:

1. An eye-tracking system for excluding pixel locations from a pupil-detection process, the eye-tracking system configured to:
   receive image-data comprising a plurality of pixel-arrays, each pixel-array having a plurality of pixel locations and an intensity-value at each of the pixel locations;
   for each pixel location of a region of pixel locations:
      define an intensity-value-set comprising the intensity-values at the pixel location for two or more of the plurality of pixel-arrays; and
      determine the pixel location to be an excluded pixel location if the intensity-value-set does not satisfy an intensity condition; and
   exclude the excluded pixel locations from the pupil-detection process;
   wherein the plurality of pixel-arrays includes a historical-pixel-array and one or more image-pixel-arrays, wherein the one or more image-pixel-arrays each represent an image of an eye of a user; and
   for each pixel location in the region of pixel locations:
      the intensity-value-set comprises a historical-intensity-value and a current-image-intensity-value, wherein for a first image-pixel-array of the one or more image-pixel-arrays, the eye-tracking system is configured to:
         set the historical-intensity-value to the intensity-value of the pixel location in the historical-pixel-array;
         set the current-image-intensity-value to the intensity-value of the pixel location in the first image-pixel-array; and
         determine the pixel location as an excluded pixel location if the historical-intensity-value and the current-image-intensity-value of the intensity-value-set are less than an intensity threshold.

2. The eye-tracking system of claim 1, wherein the plurality of pixel-arrays comprises one or more image-pixel-arrays, each representing an image of an eye of a user and wherein the eye-tracking system is further configured to perform the pupil-detection process for one or more of the image-pixel-arrays or one or more corresponding images of the eye of the user.

3. The eye-tracking system of claim 1, wherein the eye-tracking system is further configured to exclude the excluded pixel locations from the pupil-detection process and perform the pupil-detection process for the first image-pixel-array or a corresponding first image of the eye of the user.

4. The eye-tracking system of claim 1, wherein for a second image-pixel-array of the one or more image-pixel-arrays, the eye-tracking system is further configured to:
   for each pixel location in the region of pixel locations:
      calculate an updated intensity-value of the pixel location in the historical-pixel-array as the greater of the historical-intensity-value and the current-image-intensity-value;

set the historical-intensity-value of the intensity-value-set to the updated intensity-value;

set the current-image-intensity-value of the intensity-value-set to the intensity-value of the pixel location in the second image-pixel-array; and determine the pixel location to be an excluded position if the historical-intensity-value and the current-image-intensity-value of the intensity-value-set are less than the intensity threshold.

5. The eye-tracking system of claim 4, wherein the eye-tracking system is further configured to repeat the process of claim 4 for subsequent image-pixel-arrays.

6. The eye-tracking system of claim 4, wherein the eye-tracking system is further configured to exclude the excluded pixel locations from the pupil-detection process and perform the pupil-detection process for the second image-pixel-array or a corresponding second image of the eye of the user.

7. The eye-tracking system of claim 6, wherein the eye-tracking system is further configured to:

for each pixel location of the region of pixel locations, determine the pixel location to be a candidate pixel location if the historical-intensity-value and the current-image-intensity-value of the intensity-value-set are greater than or equal to the intensity threshold; and include one or more of the candidate pixel locations in the pupil-detection process.

8. The eye-tracking system of claim 4, wherein the eye-tracking system is configured to adjust the updated-intensity-value by a slippage-constant prior to setting the historical-intensity-value.

9. The eye-tracking system of claim 1, wherein:

the plurality of pixel-arrays comprises a plurality of image-pixel-arrays, each representing an image of an eye of a user;

the intensity-value-set for each pixel location comprises the intensity-values at the pixel location for each of the plurality of image-pixel-arrays; and the intensity condition comprises a condition that at least one intensity-value of the intensity-value-set exceeds an intensity threshold.

10. The eye-tracking system of claim 1, wherein:

the plurality of pixel-arrays comprises a plurality of image-pixel-arrays, each representing an image of an eye of a user;

the intensity-value-set for each pixel location comprises the intensity-values at the pixel location for each of the plurality of image-pixel-arrays; and the intensity condition comprises a condition that the intensity-value-set comprises a variation in intensity-value.

11. The eye-tracking system of claim 10, wherein the condition further comprises that the variation in intensity-value exceeds a variation threshold.

12. The eye-tracking system of claim 1, wherein the region of pixel locations comprises pixel locations outside a safe region of a pixel-array.

13. The eye-tracking system of claim 12, wherein the safe region comprises a group of pixel locations in the centre of each pixel-array.

14. The eye-tracking system of claim 12, wherein the eye-tracking system is further configured to:

set a first size and/or a first position of the safe region for a first group of image-pixel-arrays; and set a second size and/or second position of the safe region for a second group of image-pixel-arrays, wherein each image-pixel-array represents an image of an eye of a user.

15. The eye-tracking system of claim 1, wherein the region of pixel locations comprises all pixel locations.

16. The eye-tracking system of claim 1, wherein the pupil-detection process comprises a sliding-window based algorithm or a regressor based algorithm.

17. A head-mounted device comprising the eye-tracking system of claim 1.

18. A method for excluding pixel locations from a pupil-detection process, the method comprising:

receiving image data comprising a plurality of pixel-arrays, each pixel-array having a plurality of pixel locations and an intensity-value at each of the pixel locations;

for each pixel location of a region of pixel locations:

defining an intensity-value-set comprising the intensity-values at the pixel location for two or more of the plurality of pixel-arrays; and determining the pixel location to be an excluded pixel location if the intensity-value-set does not satisfy an intensity condition; and excluding the excluded pixel locations from the pupil-detection process;

wherein the plurality of pixel-arrays includes a historical-pixel-array and one or more image-pixel-arrays, wherein the one or more image-pixel-arrays each represent an image of an eye of a user; and for each pixel location in the region of pixel locations:

the intensity-value-set comprises a historical-intensity-value and a current-image-intensity-value, wherein for a first image-pixel-array of the one or more image-pixel-arrays, the eye-tracking system is configured to:

set the historical-intensity-value to the intensity-value of the pixel location in the historical-pixel-array;

set the current-image-intensity-value to the intensity-value of the pixel location in the first image-pixel-array; and determine the pixel location as an excluded pixel location if the historical-intensity-value and the current-image-intensity-value of the intensity-value-set are less than an intensity threshold.

19. One or more non-transitory computer-readable storage media storing computer-executable instructions that, when executed by a computing system, causes the computing system to perform the method of claim 18.

* * * * *